United States Patent
Itzkovich et al.

(10) Patent No.: US 12,089,928 B2
(45) Date of Patent: Sep. 17, 2024

(54) DEVICE, SYSTEM AND METHOD FOR NON-INVASIVE MONITORING OF PHYSIOLOGICAL MEASUREMENTS

(71) Applicant: WEAR2B LTD., Rosh Pina (IL)

(72) Inventors: Mordechai Itzkovich, Petach Tikva (IL); Ohad Bashan, Sde Varburg (IL); Giora Bar-Sakai, Tel Aviv (IL); Oded Bashan, Rosh Pina (IL)

(73) Assignee: Wear2B Ltd., Rosh Pina (IL)

( * ) Notice: Subject to any disclaimer, the term of this patent is extended or adjusted under 35 U.S.C. 154(b) by 94 days.

(21) Appl. No.: 16/612,383

(22) PCT Filed: May 17, 2018

(86) PCT No.: PCT/IL2018/050540
§ 371 (c)(1),
(2) Date: Nov. 10, 2019

(87) PCT Pub. No.: WO2018/211512
PCT Pub. Date: Nov. 22, 2018

(65) Prior Publication Data
US 2020/0196918 A1    Jun. 25, 2020

Related U.S. Application Data

(60) Provisional application No. 62/507,831, filed on May 18, 2017.

(51) Int. Cl.
*A61B 5/1455* (2006.01)
*A61B 5/00* (2006.01)
*A61B 5/145* (2006.01)

(52) U.S. Cl.
CPC ............ *A61B 5/1455* (2013.01); *A61B 5/002* (2013.01); *A61B 5/14532* (2013.01); *A61B 5/7221* (2013.01); *A61B 5/7275* (2013.01)

(58) Field of Classification Search
CPC ... A61B 5/1455; A61B 5/002; A61B 5/14532; A61B 5/7221; A61B 5/7275
See application file for complete search history.

(56) References Cited

U.S. PATENT DOCUMENTS

| | | | |
|---|---|---|---|
| 6,482,441 B1 | 11/2002 | Hasegawa et al. | |
| 6,615,061 B1 * | 9/2003 | Khalil | A61B 5/14532 600/316 |

(Continued)

FOREIGN PATENT DOCUMENTS

| | | |
|---|---|---|
| CN | 101926775 | 12/2010 |
| CN | 105636511 | 6/2016 |

(Continued)

OTHER PUBLICATIONS

Search Report for European Patent Application No. 18803032.4, mailed on Jan. 12, 2021.

(Continued)

*Primary Examiner* — Eric F Winakur
(74) *Attorney, Agent, or Firm* — PEARL COHEN ZEDEK LATZER BARATZ LLP (57) ABSTRACT

A non-invasive monitoring device for monitoring physiological condition of a subject may include at least one light source for emitting light at at least one predetermined narrow spectral wavelength band onto a living tissue of the subject and two or more light sensors. Each of the two or more light sensors may correspond to a specific substance in a living tissue of the subject and may be configured to measure a change in a concentration of the specific substances to which the sensor corresponds. The distance of each of the two or more sensors from the light source, may be determined so that intensity of light scattered by each specific substance, may have a maximal signal to noise ratio at the determined distance of the corresponding sensor.

12 Claims, 6 Drawing Sheets

(56) References Cited

U.S. PATENT DOCUMENTS

| | | |
|---|---|---|
| 7,807,188 B2 | 10/2010 | Hoath et al. |
| 9,448,165 B2 | 9/2016 | Gulati et al. |
| 2002/0026106 A1 | 2/2002 | Khalil et al. |
| 2002/0130430 A1 | 9/2002 | Castor |
| 2003/0194443 A1 | 10/2003 | Yano et al. |
| 2004/0039287 A1 | 2/2004 | Horiuchi et al. |
| 2006/0233883 A1 | 10/2006 | Ishihara et al. |
| 2010/0247668 A1 | 9/2010 | Eliasof et al. |
| 2014/0039284 A1 | 2/2014 | Niwayama et al. |
| 2015/0011850 A1 | 1/2015 | Ruchti et al. |
| 2015/0216425 A1 | 8/2015 | Gladshtein et al. |
| 2016/0151012 A1 | 6/2016 | Bozkurt et al. |
| 2016/0183813 A1* | 6/2016 | Naima ............... A61B 5/0537 600/479 |
| 2016/0270672 A1 | 9/2016 | Chen et al. |
| 2018/0238794 A1 | 8/2018 | Kangas et al. |

FOREIGN PATENT DOCUMENTS

| | | |
|---|---|---|
| DE | 1020070621130 | 6/2009 |
| FR | 2827767 | 1/2003 |
| JP | 2005-213170 | 8/2005 |
| JP | 2006-321763 | 11/2006 |
| JP | 2008-024658 | 2/2008 |
| JP | 2010-150151 | 7/2010 |

OTHER PUBLICATIONS

EP Office Action from corresponding EP Application No. 12 707 143.9, mailed on Apr. 13, 2015.

PCT International Search Report and Written Opinion from corresponding PCT Application No. PCT/IL2012/050020, mailed Oct. 29, 2012.

PCT International Search Report and Written Opinion from corresponding PCT Application No. PCT/IL2018/050540, mailed Sep. 6, 2018.

Chinese Office Action for Application No. 2018800473374, mailed on Dec. 9, 2021.

* cited by examiner

DEVICE, SYSTEM AND METHOD FOR NON-INVASIVE MONITORING OF PHYSIOLOGICAL MEASUREMENTS

CROSS-REFERENCE TO RELATED APPLICATIONS

This application is a National Phase Application of PCT International Application No. PCT/IL2018/050540, International Filing Date 17 May 2018, entitled, "DEVICE, SYSTEM AND METHOD FOR NON-INVASIVE MONITORING OF PHYSIOLOGICAL MEASUREMENTS", claiming the benefit of U.S. Provisional Patent Application No. 62/507,831, filed 18 May 2017, which is hereby incorporated by reference.

FIELD OF THE INVENTION

The present invention generally relates to non-invasive physiological measurements. More particularly, the present invention relates to wearable devices, systems and methods for non-invasive monitoring and analyzing of physiological measurements.

BACKGROUND OF THE INVENTION

Many people periodically undergo physical checks in order to monitor any change in their health. For instance, checks may include taking periodic (e.g., monthly, quarterly) blood tests to check cholesterol levels in the blood, or daily glucose tests with a dedicated device (typically requiring skin puncturing) so as to monitor the glucose levels in the blood.

Since these tests may be invasive and sometimes painful to the patient, a need arises for a non-invasive solution that could allow users to continuously monitor their physiological characteristics as well as identify trends and changes in the levels of the measured parameters in the blood. Some commercially available products allow non-invasive measurements of physiological signs such as pulse or temperature, however these solutions are not very accurate and there is no available solution to replace the current invasive measurements, capable of measuring levels of blood components in a non-invasive manner.

Quantitation of spectroscopy data using the Beer-Lambert law (relating to attenuation of light to the properties of the material through which light travels) requires that the optical path length is known. In near infra-red spectroscopy (NIRS), light scattering by the tissues means that not all the light that enters the tissues is detected, and even the detected light has travelled along a distribution of paths. A modified Beer-Lambert law can be applied to quantify changes in chromophore concentration as function of time (t) from the measured changes in tissue attenuation. This modified law uses the differential path length $<L(\lambda,t)>$ which is defined as the local gradient of the attenuation versus the absorption coefficient of the tissue. As used herein $<L(\lambda,t)>$ is the average distance the detected light has traveled in the tissue. The farther the light is travel in the tissue the deeper its penetrates. Thus $<L(\lambda,t)>$ is correlated to D—the depth from the skin surface) $<L(\lambda,t)>$ is affected by the changes in chromophore concentration as a function of time.

Changes in the detected optical density is usually approximated by modified Beer-Lambert law with:

$$\Delta OD(\lambda, t) = -\ln\left(\frac{I(\lambda, t)}{I_0(\lambda)}\right) \approx <L(\lambda, t)> \Delta\mu_a(\lambda, t) + \left(\frac{\mu_a^0(\lambda)}{\mu_s'^0(\lambda)}\right) <L(\lambda, t)> \Delta\mu_s'(\lambda, t) \quad (1)$$

Where '$\lambda$' is the wavelength, 't' is the time from detection start, $I_0(\lambda)$ is the baseline (at t=0) intensity detected in wavelength '$\lambda$', $I(\lambda,t)$ is the intensity detected at time 't' in wavelength '$\lambda$', $<L(\lambda,t)>$ is the differential path length that is approximately equal to the mean path length, $\mu_a^0$ is the absorption coefficient (at time t=0), $\mu_s'^0$ is the reduced scattering coefficient (at time t=0), $\Delta\mu_a(\lambda,t)$ is the change in the absorption coefficient (from time t=0 to time 't'), and $\Delta\mu_s'(\lambda,t)$ is the change in the reduced scattering coefficient (from time t=0 to time 't').

The absorption coefficient of a compound in the solution can be written as:

$$\mu_a(\lambda,t) = \Sigma_{i=1}^n \epsilon_i(\lambda) \cdot C_i(t) \quad (2)$$

Where $\epsilon_i(\lambda)$ and $C_i(t)$ are the molar absorptivity and molar concentration of a component 'i' in the media, respectively.

Thus far, the use of the differential path length has only been demonstrated to be valid for a homogeneous medium, but real organs consist of various tissue components that have different optical parameters. Therefore, for the purpose of accurate quantitation of NIRS data it is important to understand the nature of light transport through an inhomogeneous medium.

SUMMARY OF EMBODIMENTS OF THE INVENTION

Some aspects of the invention may be directed to a non-invasive monitoring device for monitoring physiological condition of a subject. In some embodiments, the device may include at least one light source for emitting light at at least one predetermined narrow spectral wavelength band onto a living tissue of the subject and two or more light sensors ($S_1, \ldots, S_n$). In some embodiments, each of the two or more light sensors ($S_1, \ldots, S_n$) may correspond to a specific substance in a living tissue of the subject and is configured to measure a change in a concentration of the specific substances to which the sensor corresponds. In some embodiments, the distance ($d_1, \ldots, d_n$) of each of the two or more sensors from the light source, may be determined so that intensity ($I_1, \ldots, I_n$) of light scattered by each specific substance, may have a maximal signal to noise ratio at the determined distance of the corresponding sensor. In some embodiments, the maximal signal to noise ratio is the ratio between the intensity of light scattered by the specific substance and all other intensities received at the corresponding sensor.

In some embodiments, the distance ($d_1, \ldots, d_n$) of each of the two or more sensors from the light source, may further determined according to the depth a layer ($L_1, \ldots, L_n$) of the living tissue in which one or more of the substances is contained. In some embodiments, the distance ($d_1, \ldots, d_n$) of each of the two or more sensors from the light source, is further determined using scattering and absorbing parameters of each substance. In some embodiments, the one or more narrow spectral wavelengths bands may be between 400-2500 nm and have a difference of 5-100 nm between the upper wavelength and the lower wavelength of each band.

In some embodiments, the non-invasive monitoring device may include a wearable housing for holding the at least one light source and the two or more light sensors. In some embodiments, the non-invasive monitoring device may include a communication unit and a controller. In some embodiments, the controller may be configured to: receive measurements of scattered light intensities received at each of the two or more light sensors and send, via the communication unit, information to a computing device. In some embodiments, the controller may further be configured to control the at least one light source to emit light; receive measurements of scattered light intensities received at each of the two or more light sensors, at an initial time ($t_0$); receive measurements of scattered light intensities received at each of the two or more light sensors, at at least one consecutive time (t); and determine a change of a concentration in time, of at least one substance in the user's tissue based on the measured light intensities.

In some embodiments, the controller may further be configured to: control the at least one light source to emit light at two or more predetermined narrow spectral wavelength bands; receive measurements of scattered light intensities received at each of the two or more light sensors at the two or more predetermined narrow spectral wavelength bands, at an initial time ($t_0$); receive measurements of scattered light intensities received at each of the two or more light sensors at two or more predetermined narrow spectral wavelength bands, at at least one consecutive time (t); and determine a change of a concentration in time, of one or more substances in the user's tissue based on the measured light intensities.

Some additional aspects of the invention may be related to system for non-invasive monitoring of a physiological condition of a subject. In some embodiments, the system may include at least one non-invasive monitoring device according to any one of the embodiments disclosed herein and a computing device configured to: receive measurements of scattered light intensities received at each of the two or more light sensors and send, via the communication unit, information to a computing device. In some embodiments, the controller may further be configured to control the at least one light source to emit light; receive measurements of scattered light intensities received at each of the two or more light sensors, at an initial time ($t_0$); receive measurements of scattered light intensities received at each of the two or more light sensors, at at least one consecutive time (t); and determine a change of a concentration in time, of at least one substance in the user's tissue based on the measured light intensities.

In some embodiments, the controller of the a computing device may further be configured to: control the at least one light source to emit light at two or more predetermined narrow spectral wavelength bands; receive measurements of scattered light intensities received at each of the two or more light sensors at the two or more predetermined narrow spectral wavelength bands, at an initial time ($t_0$); receive measurements of scattered light intensities received at each of the two or more light sensors at two or more predetermined narrow spectral wavelength bands, at at least one consecutive time (t); and determine a change of a concentration in time, of one or more substances in the user's tissue based on the measured light intensities.

Some aspects of the invention may be related to a method of non-invasive monitoring of physiological condition of a subject. In some embodiments, the method may include emitting light from a light source having at least one predetermined narrow spectral wavelengths band; measuring scattered light intensities received at each of two or more light sensors, at an initial time ($t_0$); measuring scattered light intensities received at each of the two or more light sensors, at at least one consecutive time (t); and determining a change of a concentration in time, of at least one substance in a user's tissue based on the measured light intensities. In some embodiments, each of the two or more light sensors ($S_1, \ldots, S_n$) may correspond to a specific substance in a living tissue of the subject and is configured to measure a change in a concentration of the specific substances to which the sensor corresponds. In some embodiments, the distance ($d_1, \ldots, d_n$) of each of the two or more sensors from the light source, may be determined so that intensity ($I_1, \ldots, I_n$) of light scattered by each specific substance, may have a maximal signal to noise ratio at the determined distance of the corresponding sensor. In some embodiments, the maximal signal to noise ratio is the ratio between the intensity of light scattered by the specific substance and all other intensities received at the corresponding sensor.

In some embodiments, the method may further include: controlling the at least one light source to emit light at two or more predetermined narrow spectral wavelength bands; receiving measurements of scattered light intensities received at each of the two or more light sensors at the two or more predetermined narrow spectral wavelength bands, at an initial time ($t_0$); receiving measurements of scattered light intensities received at each of the two or more light sensors at two or more predetermined narrow spectral wavelength bands, at at least one consecutive time (t); and determining a change of a concentration in time, of one or more substances in the user's tissue based on the measured light intensities.

Some additional aspects of the invention may be directed to a non-invasive monitoring device for monitoring physiological condition of a subject. In some embodiments, the device may include two or more light sources ($l_1, \ldots, l_n$) for emitting light at at least one predetermined narrow spectral wavelength band onto a living tissue of the subject and one light sensor (S). In some embodiments, each of the two or more light sources may correspond to a specific substance in a living tissue of the subject; and the one light sensor may be configured to measure a change in a concentration of the specific substances to which the light source corresponds. In some embodiments, the distance ($d_1, \ldots, d_n$) of each of the two or more light sources from the light sensor, may be determined so that intensity ($I_1, \ldots, I_n$) of light scattered by each specific substance, has a maximal signal to noise ratio at the determined distance of the corresponding light source. In some embodiments, the maximal signal to noise ratio is the ratio between the intensity of light scattered by the specific substance and all other intensities received at the corresponding sensor. In some embodiments, the distance ($d_1, \ldots, d_n$) of each of the two or more light sources from the light sensor, is further determined according to the depth a layer ($L_1, \ldots, L_n$) of the living tissue in which one or more of the substances is contained. In some embodiments, wherein the distance ($d_1, \ldots, d_n$) of each of the two or more light sources from the light sensor, is further determined according to the depth a layer ($L_1, \ldots, L_n$) of the living tissue in which one or more of the substances is contained. In some embodiments, the one or more narrow spectral wavelength bands are between 400-2500 nm and have a difference of 5-100 nm between the upper wavelength and the lower wavelength of each band In some embodiments, the non-invasive monitoring device may further include a communication unit and a controller configured to receive measurements of scattered light intensities received at the light sensor; and send, via the communication unit, information to a computing device. In some embodiments, the controller may further be configured to: control the two or more light sources to emit light; receive measurements of scattered light intensities received the light sensor, at an initial time ($t_0$); receive measurements of scattered light intensities received the light sensor, at at least one consecutive time (t); and determine a change of a concentration in time, of at least one substance in the user's tissue based on the measured light intensities.

In some embodiments, the controller may further be configured to: control the two or more light sources to emit light at two or more predetermined narrow spectral wavelength bands; receive measurements of scattered light intensities at the light sensor at the two or more predetermined narrow spectral wavelength bands, at an initial time ($t_0$); receive measurements of scattered light intensities at the light sensor at two or more predetermined narrow spectral wavelength bands, at at least one consecutive time (t); and determine a change of a concentration in time, of one or more substances in the user's tissue based on the measured light intensities.

Some other aspects of the invention may be related to: A system for non-invasive monitoring of a physiological condition of a subject. In some embodiments, the system may include at least one non-invasive monitoring device according to any one of the embodiments discloses herein and a computing device configured to: control the two or more light sources to emit light; receive measurements of scattered light intensities received the light sensor, at an initial time ($t_0$); receive measurements of scattered light intensities received the light sensor, at at least one consecutive time (t); and determine a change of a concentration in time, of at least one substance in the user's tissue based on the measured light intensities.

In some embodiments, the computing device may further be configured to: control the two or more light sources to emit light at two or more predetermined narrow spectral wavelength bands; receive measurements of scattered light intensities at the light sensor at the two or more predetermined narrow spectral wavelength bands, at an initial time ($t_0$); receive measurements of scattered light intensities at the light sensor at two or more predetermined narrow spectral wavelength bands, at at least one consecutive time (t); and determine a change of a concentration in time, of one or more substances in the user's tissue based on the measured light intensities.

Some additional aspects of the invention may be directed to a method of non-invasive monitoring of physiological condition of a subject. In some embodiments, the method may include: emitting light from two or more light sources having at least one predetermined narrow spectral wavelengths band; measuring scattered light intensities received at a light sensor, at an initial time ($t_0$); measuring scattered light intensities received at the light sensor, at at least one consecutive time (t); and determining a change of a concentration in time, of at least one substance in a user's tissue based on the measured light intensities. In some embodiments, each of the two or more light sources may correspond to a specific substance in a living tissue of the subject; and the one light sensor may be configured to measure a change in a concentration of the specific substances to which the light source corresponds. In some embodiments, the distance ($d_1, \ldots, d_n$) of each of the two or more light sources from the light sensor, may be determined so that intensity ($I_1, \ldots, I_n$) of light scattered by each specific substance, has a maximal signal to noise ratio at the determined distance of the corresponding light source In some embodiments, the maximal signal to noise ratio is the ratio between the intensity of light scattered by the specific substance and all other intensities received at the corresponding sensor. In some embodiments, the method may further include: controlling the two or more light source to emit light at two or more predetermined narrow spectral wavelength bands; receiving measurements of scattered light intensities received at the light sensor at the two or more predetermined narrow spectral wavelength bands, at an initial time ($t_0$); receiving measurements of scattered light intensities received at the light sensor at two or more predetermined narrow spectral wavelength bands, at at least one consecutive time (t); and determining a change of a concentration in time, of one or more substances in the user's tissue based on the measured light intensities.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the invention may be practiced without these specific details. In other instances, well-known methods, procedures, and components modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g. electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some aspects of the invention may be directed to a system, device and method for non-invasive monitoring of physiological condition of a subject. In some embodiments, a wearable device having one or more light sources and one or more sensors may be placed to a skin of a subject to measure changes in concentration of one or more substances (e.g., glucose, a certain protein, etc.) in the subject's tissue (e.g., blood vessel). Light emitted from the one or more light sources onto the skin of the subject, may be absorbed or penetrate and scattered from various layers of the skin. The absorption and scattering property of each layer the may depend from the composition of the layer (the concentration of the one or more substances), since different substances have different absorption and scattering properties. Furthermore, when the concentration of a particular substance in a tissue changes, so is the absorption and scattering coefficients of the tissue, as will broadly discuss below. Accordingly, a device, system and method according to some embodiments of the invention may detect light scattered from one or more layers of the skin to detect changes in the concentration of one or more substances over time. In some embodiments, the detected change may indicate a change in the physiological condition of the subject.

Figure 1A:
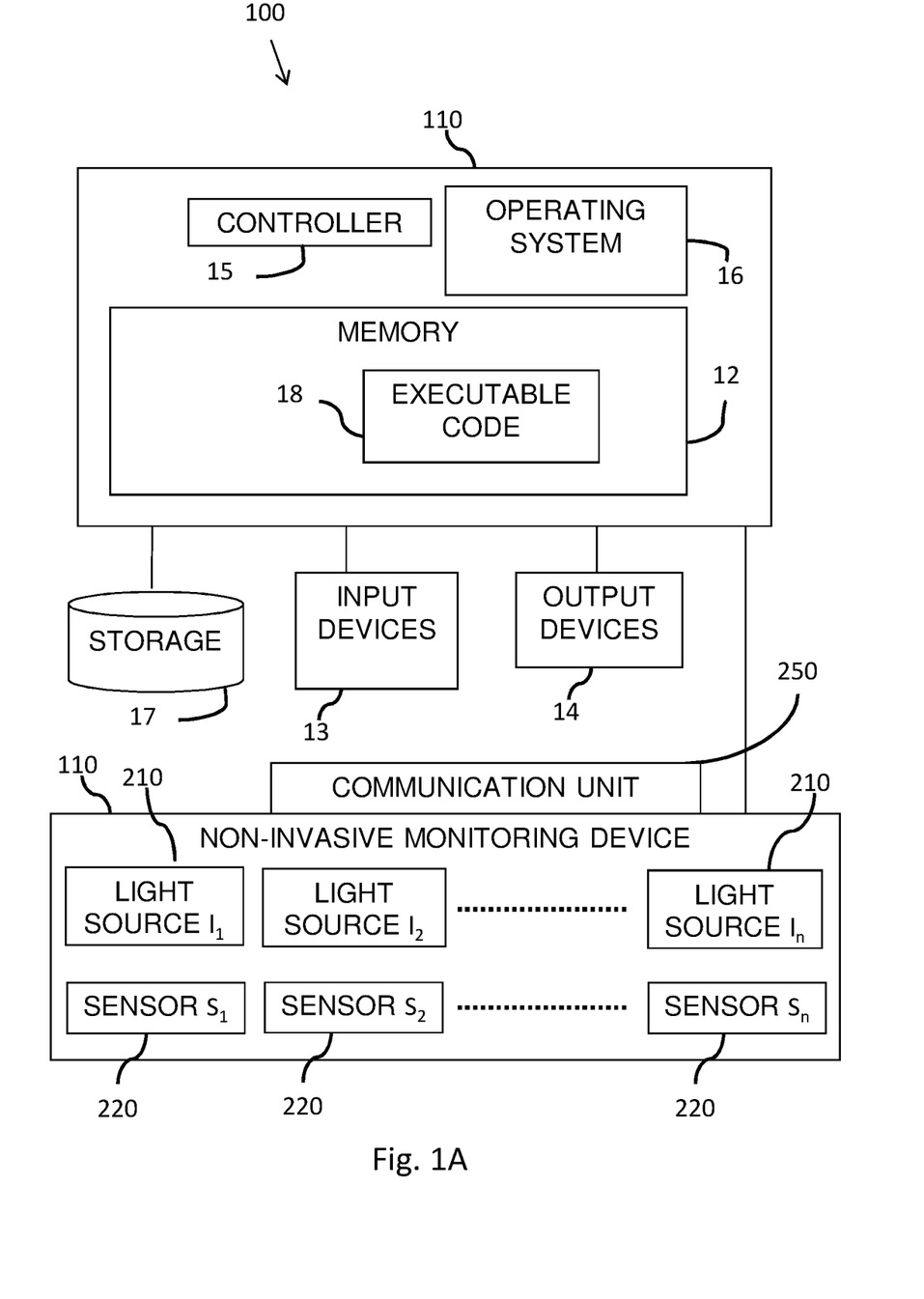
FIG. 1A shows a block diagram of an exemplary system for non-invasive monitoring of a physiological condition of a subject according to some embodiments of the present invention.

Reference is made to FIG. 1A, showing a block diagram of a system 100 for non-invasive monitoring of a physiological condition of a subject according to some embodiments of the invention. System 100 may include a computing device 11 and at least one non-invasive monitoring device 110 for monitoring of a physiological condition of a subject. Computing device 11 may be in wired or wireless communication with non-invasive monitoring device 110.

Computing device 11 may include a controller 15 that may be, for example, a central processing unit processor (CPU), a chip or any suitable computing or computational device, an operating system 16, a memory 12, a storage 17, an input device 13 and an output device 14.

Operating system 16 may be or may include any code segment designed and/or configured to perform tasks involving coordination, scheduling, arbitration, supervising, controlling or otherwise managing operation of computing device 11, for example, scheduling execution of programs. Operating system 16 may be a commercial operating system. Memory 12 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 12 may be or may include a plurality of, possibly different memory units.

Executable code 18 may be any executable code, e.g., an application, a program, a process, task or script. Executable code 18 may be executed by controller 15 possibly under control of operating system 16. Where applicable, executable code 18 may carry out operations described herein, possibly in real-time. Computing device 11 and executable code 18 may be configured to update, process and/or act upon information at the same rate the information, or a relevant event, are received. In some embodiments, more than one computing device 11 may be used. For example, a plurality of computing devices that include components similar to those included in computing device 11 may be connected to a network and used as a system.

Storage 17 may be or may include, for example, a hard disk drive, a universal serial bus (USB) device or other suitable removable and/or fixed storage unit. Content may be stored in storage 17 and may be loaded from storage 17 into memory 12 where it may be processed by controller 15. In some embodiments, some of the components shown in FIG. 1A may be omitted. For example, memory 12 may be a non-volatile memory having the storage capacity of storage 17. Accordingly, although shown as a separate component, storage 17 may be embedded or included in memory 12.

Input devices 13 may be or may include a sensor, a keyboard, a touch screen or pad or any suitable input device. It will be recognized that any suitable number of input devices may be operatively connected to computing device 11 as shown by block 13. Output devices 14 may include one or more displays, speakers and/or any other suitable output devices. It will be recognized that any suitable number of output devices may be operatively connected to computing device 11 as shown by block 14. Any applicable input/output (I/O) devices may be connected to computing device 11 as shown by blocks 13 and 14. For example, a wired or wireless network interface card (NIC), a universal serial bus (USB) device or external hard drive may be included in input devices 13 and/or output devices 14.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. For example, a storage medium such as memory 12, computer-executable instructions such as executable code 18 and a controller such as controller 15.

Some embodiments may be provided in a computer program product that may include a non-transitory machine-readable medium, stored thereon instructions, which may be used to program a computer, or other programmable devices, to perform methods as disclosed herein. Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein. The storage medium may include, but is not limited to, any type of disk including magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage devices.

A system according to embodiments of the invention may include components such as, but not limited to, a plurality of central processing units (CPU) or any other suitable multipurpose or specific processors or controllers, a plurality of input units, a plurality of output units, a plurality of memory units, and a plurality of storage units. A system may additionally include other suitable hardware components and/or software components. In some embodiments, a system may include or may be, for example, a personal computer, a desktop computer, a mobile computer, a laptop computer, a notebook computer, a terminal, a workstation, a server computer, a Personal Digital Assistant (PDA) device, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Non-invasive monitoring device 110 may include one or more one light sources ($l_1, l_2 \ldots l_n$) 210 for emitting light at at least one predetermined narrow spectral wavelength band onto a living tissue of the subject and one or more light sensors ($S_1, \ldots, S_n$) 220. In some embodiments, non-invasive monitoring device 110 may include at least one light source 210 and a plurality of light sensors ($S_1, \ldots, S_n$) 220. In such case each of the two or more light sensors 220 may correspond to a specific substance in a living tissue of the subject and may be configured to measure a change in a concentration of the specific substances to which sensor 220 corresponds. In some embodiments, the distance ($d_1, \ldots, d_n$) of each of two or more sensors 220 from light source 210, may be determined so that intensity ($I_1, \ldots, I_n$) of light scattered by each specific substance, may have a maximal signal to noise ratio at the determined distance of the corresponding sensor, as illustrated and discussed with respect to FIG. 2A.

As used herein and throughout the disclosure the maximal signal to noise ratio may be the ratio between the intensity of light scattered by the specific substance and all other intensities received at the corresponding sensor.

As used herein and throughout the disclosure the distances ($d_1, \ldots, d_n$) refers to the Euclidean distance between the geometric center of one active area of a component (e.g., a sensor/alight source) to the geometric center of the other component's active area. The active area of a sensor may include the area at which light photons are being detected and the active area of the light source may include the area from which light photons are emitted. In some embodiments, the active area center may be off centered from the geometrical center of the sensors and/or the light sources.

In some embodiments, non-invasive monitoring device 110 may include a plurality of sources ($l_1, l_2 \ldots l_n$) 210 and a single light sensor 220. In such case each of two or more light sources 210 may be located at a different distance from light sensor 220. In some embodiments, each of two or more light sources 210 may correspond to a specific substance in a living tissue of the subject; and one light sensor 220 may be configured to measure a change in a concentration of the specific substances to which light source 220 corresponds. In some embodiments, the distance ($d_1, \ldots, d_n$) of each of the two or more light sources 210 from light sensor 220, may be determined so that intensity ($I_1, \ldots, I_n$) of light scattered by each specific substance, has a maximal signal to noise ratio at the determined distance of the corresponding light source, as illustrated and discussed with respect to FIG. 2B.

In some embodiments, one or more light sources 210 may be configured to emit light at one or more narrow spectral wavelength bands. For example, the one or more narrow spectral wavelengths band may include wavelength band having a difference of between 5-100 nm between the upper and the lower wavelengths. In some embodiments, the upper and lower wavelengths at each band are between 400-2500 nm. In some embodiments, one or more light sources 210 may be or may include a point lights, such as, light emitting diode (LED), VCSEL, semiconductor lasers and the like.

In some embodiments, one or more light sensors 220 may be configured to detect light at any wavelength, for example, between 400-2500 nm. One or more light sensors 220 may be or may include, for example, photodiodes, such as InGaAs, photodiode and the like. In some embodiments, light emitted form one or more light sensors 220 may be in the Infra-Red or near Infra-Red (IR) spectrum. In some embodiments, Short Wave IR (SWIR) imaging may be utilized for measuring physiological signals from the blood of a subject. The SWIR waveband runs from the lower edge of the near IR region at 400 nm up to 2500 nm.

In some embodiments, non-invasive monitoring device 110 may further include a communication unit 250. Communication unit 250 may include any communication module that may be configured to wirelessly communicate with external processor (e.g., via Wi-Fi, Bluetooth, near field communication (NFC), etc.), such as computing device 11, mobile device 120 (illustrated in FIG. 1B) and the like. In some embodiments, non-invasive monitoring device 110 may include computing device 11.

Figure 1B:
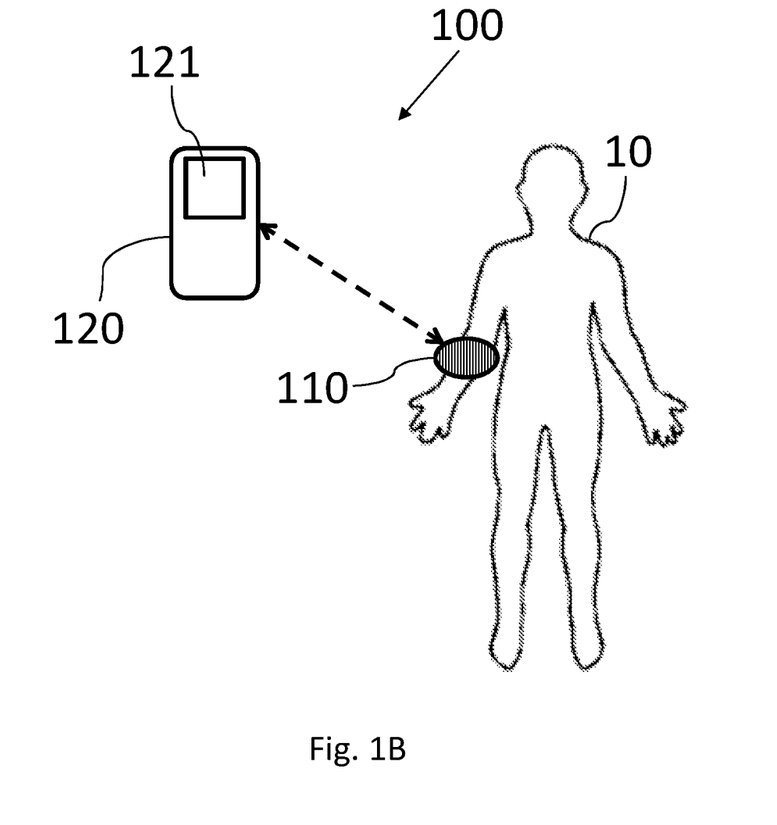
FIG. 1B schematically illustrates a block diagram of the non-invasive monitoring system, according to some embodiments of the invention.

Reference is now made to FIG. 1B, which schematically illustrates a block diagram of non-invasive monitoring system 100 according to some embodiments of the invention. It should be noted that the direction of arrows in FIG. 1B may indicate the direction of information flow. The non-invasive monitoring system 100 may allow continuous and/or repetitive non-invasive monitoring of a subject 10, using wearable monitoring device 110. In some embodiments, non-invasive monitoring system 100 may allow multi trajectory detection of spectral data in an inhomogeneous medium to extract the changes in chromophore concentration.

Non-invasive monitoring system 100 may include at least one monitoring device 110 configured to detect changes in measured physiological signals of subject 10, and a computerized device 120 (e.g., a processor such as controller 15 of computing device 11 of FIG. 1A in the vicinity of subject 10 and/or a controller in a remote facility such as a medical facility) in communication with at least one monitoring device 110. Systems and devices 100, 110 and 120 may be or include components similar to those described in FIG. 1A. The computerized device 120 may be configured to receive data (e.g., wirelessly via communication unit 250) corresponding to measured physiological signals from at least one monitoring device 110. According to some embodiments, a processor (such as controller 15 in FIG. 1A) of computerized device 120 may determine or calculate at least one physiological signal or value from detected light signals from monitoring device 110. For example, monitoring device 110 may detect scattered light beams and determine the received intensity to be sent (e.g., wirelessly) to computerized device 120 for further processing to determine at least one physiological signal (e.g., a glucose level may be determined or calculated) for example by calculating a set of equations with multiple variables for multiple wavelengths.

In some embodiments, computerized device 120 may be or may include, for example, a mobile phone, a tablet, a personal computer, a mobile computer, or any other suitable computing device 120. For example, system 100 as described herein may include one or more devices such as computerized device 120. In some embodiments, the at least one monitoring device 110 may be removably attachable to the subject's body 10. In some embodiments, the at least one monitoring device 110 may be wearable on a limb of subject 10 and/or on other parts of the subject's body (e.g. on a finger).

It should be appreciated that wearable non-invasive monitoring device 110 may continuously collect data on the physiological signals (e.g., pulse, blood substances levels, etc.) of the subject 10, as long as monitoring device 110 is worn by (or otherwise attached to) subject 10, and therefore non-invasive monitoring device 110 may provide ongoing data such that changes in measured physiological signals may be detected. In some embodiments, non-invasive monitoring device 110 may collect the data (e.g., and store in a dedicated memory) when non-invasive monitoring device 110 is worn by the subject 10 to be provided to the subject alter one to the subject even when non-invasive monitoring device 110 is not worn by the subject 10.

According to some embodiments, the monitored data may be transferred from computerized device 120 to wearable monitoring device 110, and vice versa, via communication unit 250 (e.g., via Wi-Fi, Bluetooth, near field communication (NFC), etc.). For example, a subject 10 wearing monitoring device 110 and also operating a mobile phone, may utilize the mobile phone as computerized device 120 in order to transfer data to and from wearable monitoring device 110 via wired and/or wireless communication.

In some embodiments, wearable monitoring device 110 may include a measuring unit (200 in FIGS. 2A and 2B) with a dedicated controller that may be configured to measure physiological signs of subject 10, and a power storage unit (e.g. a battery not illustrated). For instance, computerized device 120 may include a compatible communication module, a display (e.g. with a user interface), and a processor capable of processing and monitoring the physiological data of subject 10 measured by monitoring device 110.

Computerized device 120 may have, according to some embodiments, a dedicated user interface (e.g. with a dedicated algorithm installed thereon) so as to display real-time measurements to subject 10. Thus, users (e.g., the subject, a caregiver and/or physician) may receive alerts and/or updates regarding the physiological signs that were measured by the wearable monitoring device 110. In some embodiments, computerized device 120 may issue an alert (e.g., via display and/or speaker 121) upon detection of a change in measured physiological signals exceeding a predetermined threshold.

Figure 2A:
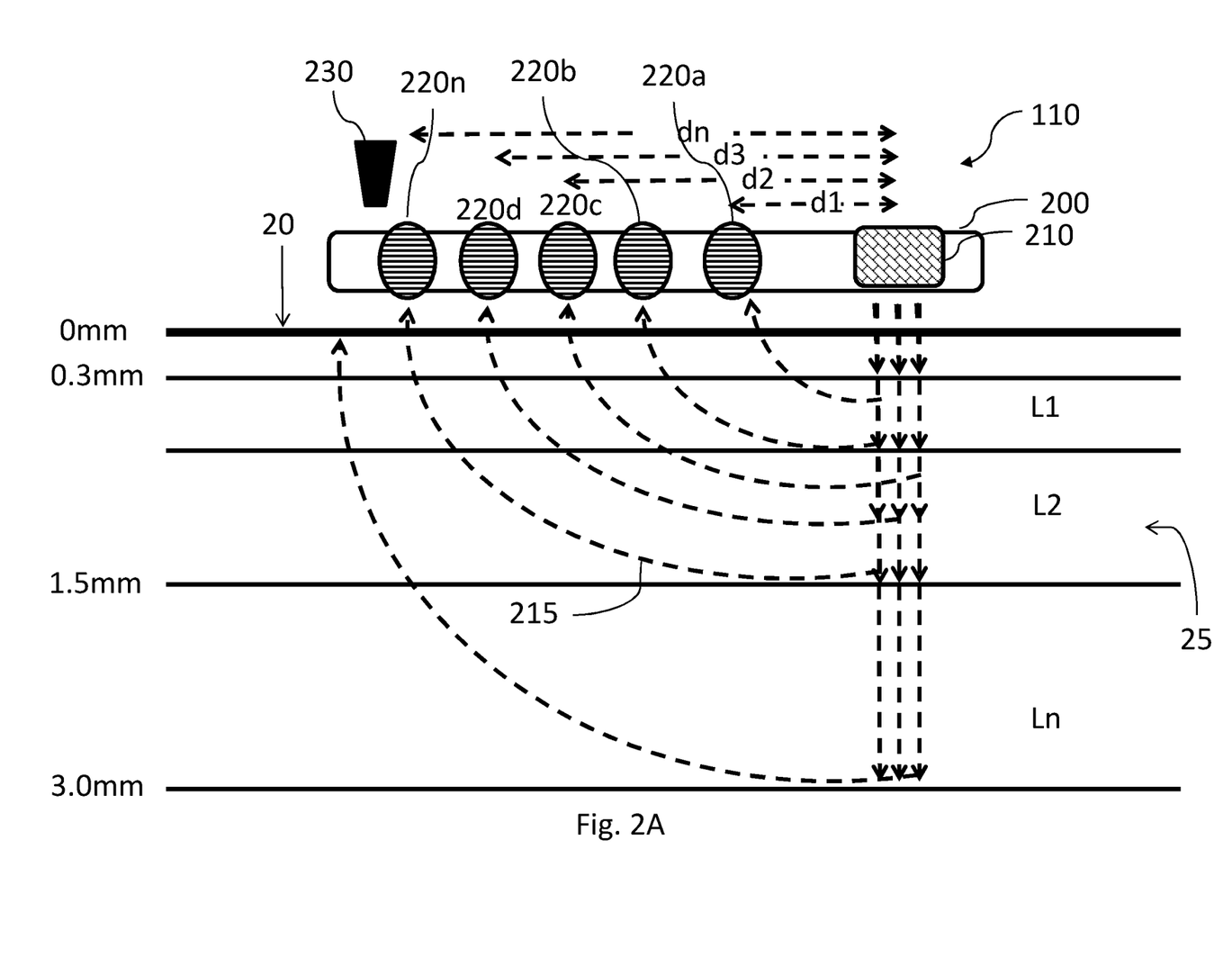
FIGS. 2A and 2B schematically illustrate cross-sectional views of non-invasive monitoring devices for monitoring physiological condition of a subject according to some embodiments of the invention.
Figure 2B:
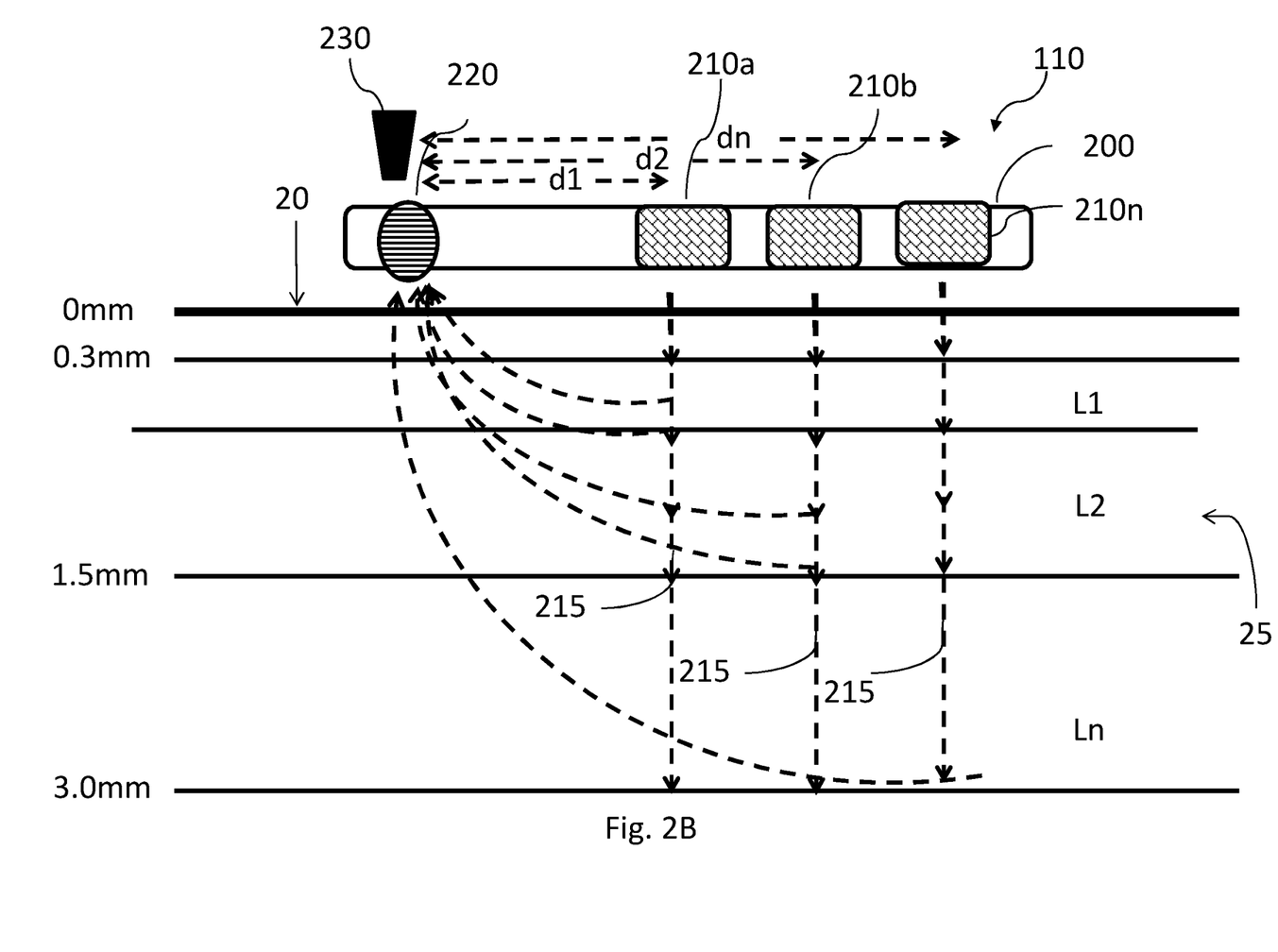

Reference is now made to FIGS. 2A and 2B which are illustrations of non-invasive monitoring devices for monitoring physiological condition of a subject according to some embodiments of the invention. Device 110 may be attached to skin 20 of subject 10. In some embodiments, the direction of dashed arrows may indicate the direction of the light beams progress.

As may be apparent to one of ordinary skill in the art, light in specific narrow spectral wavelength band (e.g., a band of 5-100 nm) between 400-2500 nm may be reflected/scattered from tissues of the subject's body. For example, narrow spectral wavelength band may include wavelength bands 475-480 nm, 500-525 nm, 1000-1010 nm, 1300-1320, 1450-1455, 1800-1900 nm and the like. In some embodiments, the light may be reflected/scattered from subcutaneous tissue (e.g. reflected/scattered from blood inside a blood vessel). In some embodiments, the light may be reflected/scattered from tissue above a blood vessel and may have different intensities since light reflected/scattered from tissue above a blood vessel may have a weaker reflection/scattering due to higher light absorption in water content.

In some embodiments, different substances in the blood (in an inhomogeneous medium) may have different light absorption/scattering coefficients as function of wavelength. Accordingly, in order to use light scattered/absorbed by a specific substances it is essential to ensure that the collected light (e.g., by a light sensor $220a$, $220b$ . . . $220n$) has maximal signal to noise ratio and has been received from a tissue (e.g., skin layer $L_1$, . . . , $L_n$) that includes the substance. Since light emitted from one or more light source ($210a$, $210b$ . . . $210n$) onto the subject's tissue 20 scattered at various directions only a small portion of that light can be collected by a sensor located at a distance d from the light source. It was found that at different distances ($d_1$, . . . , $d_n$) between light source 210 and sensor 220 (for the same wavelength), light scattered from different layers or scattered by different biochemical substances within a layer may be received at high signal to noise ratio.

Accordingly, in order to collect light from scattered by a specific biochemical substance contained in a specific layer (e.g., $L_2$) at maximal signal to noise ratio a corresponding distance ($d_2$) between the sensor and the light source may be determined. In some embodiments, since the scattering from each layer depends from the biochemical composition of the layer (i.e., the substances contained in the layer), in order to collect light scattered from two different substances, two distances between two sensors and a single light source or two light sources and a single sensor may be determined (for example, $d_2$ and $d_3$ illustrated in FIG. 2A). Each of the determined distances may determine such that light scattered from a specific substance in the layer may be received in the sensor (or sensors) at maximal signal to noise ratio at the corresponding sensor. Accordingly, in order to detect the presence of 5 substances at least 5 sensors and/or at least 5 light sources may be included in device 110.

Additionally, or alternatively, different wavelength ($\lambda_1$, $\lambda_2$ . . . $\lambda_n$) may be used to collect light scattered from different substances. Different wavelength scattered differently from different substances. Accordingly, the wavelengths emitted from one or more sensors may each be determined such that light scattered from a specific substance may be collected by the one or more sensors at maximal signal to noise ratio at the corresponding sensor.

In some embodiments, computer simulations of the path of light through various layers of a tissue (e.g., skin) <L($\lambda$,t)> have been conducted, using for example, Monte Carlo simulation. The computer simulations were conducted to find optimal distances between light sources and sensors that may ensure light scattered from a specific substance to be collected at maximal signal to noise ratio. The computer simulations may further be use to find the optimal wavelength (or narrow wavelength band) to collect light scattered from a specific substance at maximal signal to noise ratio.

In some embodiments, measuring unit 200 of devices 110 designed to collect light scattered from specific substances may collect light intensities to be processed by a controller such as controller 15, computerized device 120 and the like. In some embodiments, a set of equations with multiple variables (or light absorption/scattering coefficients) may be created based on the scattered light readings, received in sensors 220 by illuminating a tissue 25 of subject 10 (e.g., a blood vessel) with one or more wavelengths, such that the set of equations may be solved in order to find a change in the concentration of one or more substance in the blood. For example, each such equation may correspond to a different substance in the blood and/or correspond to a different wavelength. Once changes in the light absorption/scattering coefficients may be determined, it may be possible to determine changes in the concentration of a substance in blood (e.g., glucose) by illuminating a tissue with a wavelength corresponding to a known light absorption/scattering coefficient. For example, determining changes in the coefficients of seven different substances by performing measurements with at least seven different wavelengths ($\lambda_1$, $\lambda_2 \ldots \lambda_7$) and/or seven different distances ($d_1$, $d_2 \ldots d_7$).

According to the modified Beer-Lambert law, for 'm' components and 'n' wavelengths:

$$\begin{bmatrix} \mu_a(\lambda_1, t) \\ \vdots \\ \mu_a(\lambda_n, t) \end{bmatrix}_{n \times 1} = \begin{bmatrix} \epsilon_1(\lambda_1) & \cdots & \epsilon_m(\lambda_1) \\ \vdots & \vdots & \vdots \\ \epsilon_1(\lambda_n) & \cdots & \epsilon_m(\lambda_n) \end{bmatrix}_{n \times m} \cdot \begin{bmatrix} C_1(t) \\ \vdots \\ C_m(t) \end{bmatrix}_{m \times 1} \quad (3)$$

A change of the molar concentration of one of the compounds $\Delta C_i(t)$ may cause a change in the absorption coefficient: $\mu_a$ $$\Delta \mu_a(\lambda, t) = \Sigma_{i=1}^{m} \epsilon_i(\lambda) \cdot \Delta C_i(t) \quad (4)$$

or in matrix form:

$$\begin{bmatrix} \Delta \mu_a(\lambda_1, t) \\ \vdots \\ \Delta \mu_a(\lambda_n, t) \end{bmatrix}_{n \times 1} = \begin{bmatrix} \epsilon_1(\lambda_1) & \cdots & \epsilon_m(\lambda_1) \\ \vdots & \vdots & \vdots \\ \epsilon_1(\lambda_n) & \cdots & \epsilon_m(\lambda_n) \end{bmatrix}_{n \times m} \cdot \begin{bmatrix} \Delta C_1(t) \\ \vdots \\ \Delta C_m(t) \end{bmatrix}_{m \times 1} \quad (5)$$

Based on the modified Beer-Lambert law, the optical density change at the output due to the changes in the molar concentration changes in homogenous medium may be calculated as:

$$\begin{bmatrix} \Delta OD_a(\lambda_1, t) \\ \vdots \\ \Delta OD_a(\lambda_n, t) \end{bmatrix}_{n \times 1} = L \cdot \begin{bmatrix} \Delta \mu_a(\lambda_1) \\ \vdots \\ \Delta \mu_a(\lambda_n) \end{bmatrix}_{n \times 1} \quad (6)$$

The scattering coefficient may be calculated as a product of the media scattering coefficient and the media content $$\mu'_s(\lambda, t) = \epsilon_s(\lambda) \cdot C_s(t) \quad (7)$$

The change in the scattering coefficient due to the changes in the media content may be calculated as:

$$\Delta \mu'_s(\lambda, t) = \epsilon_s(\lambda) \cdot \Delta C_s(t) \quad (8)$$

Thus, the total change in the optical density due to attenuation and scattering in homogenous medium may be calculated as:

$$\begin{bmatrix} \Delta OD(\lambda_1, t) \\ \vdots \\ \Delta OD(\lambda_n, t) \end{bmatrix}_{n \times 1} = L \cdot \begin{bmatrix} \Delta \mu_a(\lambda_1) + \Delta \mu'_s(\lambda_1) \\ \vdots \\ \Delta \mu_a(\lambda_n) + \Delta \mu'_s(\lambda_1) \end{bmatrix}_{n \times 1} \quad (9)$$

For heterogeneous medium layered structure, the modified Beer-Lambert law is still applicable to each of the components of the heterogeneous medium, and the total optical density change is the sum of the attenuation and scattering changes of each component. For 'k' layered medium detected at 'm' wavelengths the change in the optical density may be calculated as:

$$\begin{bmatrix} \Delta OD_1(t) \\ \vdots \\ \Delta OD_k(t) \end{bmatrix}_{k \times 1} = \begin{bmatrix} L_1(\lambda_1) & \cdots & L_1(\lambda_1) \\ \vdots & \vdots & \vdots \\ L_k(\lambda_n) & \cdots & L_k(\lambda_m) \end{bmatrix}_{k \times m} \cdot \begin{bmatrix} \Delta \mu_a(\lambda_1, t) + \Delta \mu'_s(\lambda_1, t) \\ \vdots \\ \Delta \mu_a(\lambda_m, t) + \Delta \mu'_s(\lambda_m, t) \end{bmatrix}_{m \times 1} \quad (10)$$

In some embodiments, the changes in the optical absorption and scattering coefficients and from it the molar concentration changes may be expressed by:

$$\begin{bmatrix} L_1(\lambda_1) & \cdots & L_k(\lambda_1) \\ \vdots & \vdots & \vdots \\ L_1(\lambda_m) & \cdots & L_k(\lambda_m) \end{bmatrix}_{k \times m}^{-1} \cdot \begin{bmatrix} \Delta OD(\lambda_1, t) \\ \vdots \\ \Delta OD(\lambda_{1m}, t) \end{bmatrix}_{m \times 1} = \begin{bmatrix} \Delta \mu_{a1}(t) + \Delta \mu'_{s1}(t) \\ \vdots \\ \Delta \mu_{ak}(t) + \Delta \mu'_{sk}(t) \end{bmatrix}_{k \times 1}$$

Where $\Delta OD(\lambda_j, t)$ is the measured optical density changing at $\lambda_j$ ($j=1 \ldots m$) at time 't'. $\Delta OD_j(t)$ in equation 10 is the measured optical density at the layer j ($j=1 \ldots k$) at time 't'. $\Delta \mu_{aj}(t)$ and $\Delta \mu'_{sj}(t)$ ($j=1 \ldots k$) in equation 11 are the changes of the absorption and reduced scattering coefficients respectively at the layer k at time t within the range of measurements ($\lambda_{min} - \lambda_{max}$).

Reference is now made to FIG. 2A which is an illustration of non-invasive monitoring device 110 for monitoring physiological condition of a subject according to some embodiments of the invention. In some embodiments, measuring unit 200 may include at least one light emitting source 210 (e.g., a point light source), for example, a light emitting diode (LED), Semiconductor Laser, VCSEL, and the like, configured to emit light beams 215 in at least one predetermined narrow spectral wavelength band. In some embodiments, the measuring unit 200 may be removably attachable to tissue 20 (e.g., skin) of the subject 10, so as to emit light beams 215 with the at least one light emitting source 210 onto tissue 20. For example, measuring unit 200 may be positioned along a sub-tissue (e.g., blood vessel 25), for example, on the wrist of the subject 10. Several layers ($L_1, \ldots, L_n$) may be identified below tissue 20 of the subject 10, for example Epidermis layer at 0.3 mm depth, a Dermis layer at 1.5 mm depth and a Subcutaneous layer there below. In some embodiments, device 110 may include a wearable housing (not illustrated) for holding at least one light source 210 and two or more light sensors 220a-220n.

In some embodiments, in order to allow simultaneous measurements of different substances (e.g. glucose, insulin, low density lipoprotein (LDL), very-low density lipoprotein (VLDL) and Albumin) the distances ($d_1, \ldots, d_n$) of each of two or more sensors 220a-220n may be determined such that each sensor detects light scattered from a corresponding substance. In some embodiments, each of the two or more light sensors 220a-220n may correspond to a specific substance in a living tissue of the subject and is configured to measure a change in a concentration ($C_1 \ldots C_n$) of the specific substances to which the sensor corresponds. For example, in order to detect changes over time in the concentration of two substances (e.g. glucose, insulin) in blood vessel 25, light emitted from light source 210 and received at sensors 220c and 220d may be proceeded (e.g., by controller 15) to determine changes over time in the concentration of the two substances.

In some embodiments, the distance ($d_1, \ldots, d_n$) of each of two or more sensors 220a-220n from light source 210, may be determined so that intensity ($I_1, \ldots, I_n$) of light scattered by each specific substance, may have a maximal signal to noise ratio at the determined distance of the corresponding sensor. In some embodiments, the maximal signal to noise ratio is the ratio between the intensity of light scattered by the specific substance and all other intensities received at the corresponding sensor.

In some embodiments, the distance ($d_1, \ldots, d_n$) of each of two or more sensors 220a-220n from light source 210, may further determined according to the depth a layer ($L_1, \ldots, L_n$) of the living tissue in which one or more of the substances is contained. In some embodiments, the distance ($d_1, \ldots, d_n$) of each of two or more sensors 220a-220a from light source 210, may further determined using scattering and absorbing parameters of each substance ($\mu_{a1} \ldots \mu_{an}$) and ($\mu_{s1} \ldots \mu_{sn}$).

In some embodiments, different light sources 210a-210n may emit light indifferent narrow spectral wavelength bands, for instance in order to allow simultaneous measurements of different substances (e.g. glucose, insulin, low density lipoprotein (LDL), very-low density lipoprotein (VLDL) and Albumin) and/or to determine the ratio between measurements of different wavelengths. In some embodiments, a single light source 210 may emit light in a plurality of narrow spectral wavelength bands. In some embodiments, measurements of different substances (e.g. glucose and Albumin) may be carried out with different narrow spectral wavelength bands and/or different sensors. In some embodiment, each light emitting source 210, or sub-sets (e.g. pairs, triplets etc.) of light emitting sources 210a-210n (illustrated for example, in FIG. 2B) may emit light in a different predetermined narrow spectral wavelength band. In some embodiments, the number of different narrow spectral wavelength bands may be determined based on the substance to be measured (e.g., two different narrow spectral wavelength bands to measure glucose). For example, a user may select to measure glucose, and thus a first number of narrow spectral wavelength bands is automatically selected by the processor, and for measurement of a different substance a second number of wavelengths is automatically selected (e.g., based on previously carried out calibration).

The light emitted from the at least one light emitting source 210 (e.g. LED) may be, according to some embodiments, in the Infra-Red or near Infra-Red (IR) spectrum. In some embodiments, Short Wave IR (SWIR) imaging may be utilized for measuring physiological signals from the blood of subject 10. The SWIR waveband runs from the lower edge of the near IR region at 400 nm up to 2500 nm and may be utilized for inspection of blood and blood components in blood vessels of the subject 10. It should be noted that if required, the range of the SWIR waveband may be increased. In some embodiment, each light emitting source 210, or sub-set of light emitting sources 210, may emit light in a different time and/or in a different frequency, such that not all light emitting sources 210 emit light simultaneously.

It should be noted that with light beams emitted from the at least one light emitting source 210 towards subject 10, the wearable monitoring device 110 may perform optical measuring (e.g. with at least one sensor 220) that are non-invasive to gather measurements.

Reference is now made to FIG. 2B which is an illustration of non-invasive monitoring device 110 for monitoring physiological condition of a subject according to some embodiments of the invention. In some embodiments, measuring unit 200 may include two or more light source 210a-210n, for example a light emitting diodes (LED), configured to emit light beams 215 in at least one predetermined narrow spectral wavelength band. In some embodiments, light beams 215 emitted from light sources 210a-210n may be received at at least one sensor 220. In some embodiments, each of two or more light sources 210a . . . 210n may correspond to a specific substance in a living tissue of the subject; and light sensor 220 may be configured to measure a change in a concentration ($C_1 \ldots C_n$) of the specific substances to which the light source corresponds. In some embodiments, the distance ($d_1, \ldots, d_n$) of each of two or more light sources 210a . . . 210n from light sensor 210, may be determined so that intensity ($I_1, \ldots, I_n$) of light scattered by each specific substance, has a maximal signal to noise ratio at the determined distance of the corresponding light source. In some embodiments, the maximal signal to noise ratio is the ratio between the intensity of light scattered by the specific substance and all other intensities received at the corresponding sensor. In some embodiments, the distance ($d_1, \ldots, d_n$) of each of two or more light sources 210a . . . 210n from the light sensor, may further be determined according to the depth a layer ($L_1, \ldots, L_n$) of the living tissue in which one or more of the substances is contained. In some embodiments, wherein the distance ($d_1, \ldots, d_n$) of each of two or more light sources 210a . . . 210n from light sensor 220, may further be determined according to the depth a layer ($L_1, \ldots, L_n$) of the living tissue in which one or more of the substances is contained In some embodiments, the measuring unit 200 may be removably attachable to tissue (e.g., skin) 20 of the subject 10, so as to emit light beams 215 with the at least one light emitting source 210 onto the skin 20. For example, measuring unit 200 may be positioned along a sub-tissue (e.g., blood vessel 25), for example, on the wrist of the subject 10. Several layers ($L_1, \ldots, L_n$) may be identified below tissue 20 of the subject 10 as disclosed herein above. In some embodiments, device 110 may include a wearable housing (not illustrated) for holding at two or more light sources 210a-210n and at least one light sensors 220.

In some embodiments, different light sources 210a-210n may emit light in different narrow spectral wavelength bands, for instance in order to allow simultaneous measurements of different substances, as disclosed herein above.

According to some embodiments, to solve this linear set of equations the optical path for each layer $L_i$ (i=1 . . . k) should be known from the light emitting source 210 to sensors 220 and for each detected wavelength. In some embodiments, the path-lengths matrix may be extracted numerically by using Monte-Carlo simulations of the optical trajectory between the light emitting source 210 and sensor(s) 220. Thus, such measurement enables detection of the optical density OD($\lambda$,t) and calculating $\Delta$OD as function of time and wavelengths in multiple trajectories between one or more light emitting sources 210a-210n and one or more sensor(s) 220a-220n.

As may be apparent to one of ordinary skill in the art, a sensor 220 having an increased distance (compared to other sensors) between a light emitting source 210 and the sensor 220 may detect light beams 215 reflected from subcutaneous tissue within the subject's body 10. In some embodiments, detection of light beams 215 reflected from deeper tissue within the subject's body 10, with known distance ('d') between each sensor 220 and at least one light emitting source 210, may allow detection of light beams 215 reflected from a blood vessel 25. In some embodiments, distance 'd' of each sensor may correspond to penetration depth of light beams 215 within the subject's body 10. It should be noted that deeper subcutaneous tissue may correspond to a blood vessel, for example during calibration light paths passing through blood vessels for each sensor 220 may be determined.

In some embodiments, measurements with a light emitting source 210 and multiple sensors 220 may provide the ability to assess a change (in time) in the molar concentration $\Delta C_i(t)$ of some of the substance media in at least one layer $L_i$ (i=1 ... k) or volume elements along the trajectory between the light emitting source 210 and the sensor(s) 220.

According to some embodiments, at least one light emitting source 210 may emit light beams 215 onto the tissue (e.g., skin) 20 of the subject 10, to be reflected/scattered from sub-tissue 25 (e.g., by the content of the blood vessel) and then received by at least one sensor 220. In some embodiments, the light beams may be transmitted through the subcutaneous tissue (including the blood vessels therein) of the subject 10 and then received by the sensor 220.

According to some embodiments, the at least one non-invasive monitoring device 110 may include a controller 230 (e.g., processor or controller 15 as shown in FIG. 1A), coupled to the measuring unit 200, and configured to measure and/or analyze physiological signs of the subject 10. In some embodiments, controller 230 may monitor physiological condition of subject 10 based on the detected light beams 215 and also based on at least one predetermined narrow spectral wavelength band, for example by solving a set of equations as described herein According to some embodiments, it may be possible to determine a light intensity threshold based on the reflection readings in one or more sensors 220, wherein the position of the measuring unit 200 being over a blood vessel may be determined according to the determined threshold so that when the reflected/scattered light has an intensity that is higher/lower than the threshold the measuring unit 200 may not be over a blood vessel.

In some embodiments, the monitoring system 100 may further include positioning correction indicators that are adapted to allow the user to correctly place measuring unit 200 over a blood vessel. For instance, displaying to the user how to move monitoring device 110 to improve positioning of light emitting sources 210 and/or sensors 220 to optimize reflections to the sensor.

In some embodiments, the difference in the data between the emitted beam and the received (reflected/scattered) beam may provide an indication on the radiation (e.g., light) absorption/scattering by the blood in blood vessel 25 and thus may indicate characteristics and blood measurements of the blood inside blood vessel 25, in a non-invasive procedure. In some embodiments, each light emitting source 210 may be provided with an optical collimator (or reflector) so as to allow directing the light beam emitted by each light source 210 in a specific predefined direction.

For example, such measurements may provide an indication for a "health matrix" with continuous glucose monitoring, dehydration monitoring, blood lipids, vitamins, calories, pulse, PWV (Pulse wave velocity) blood pressure, and also an indication of medications, pharmaceuticals and other chemicals in the blood stream of the subject. It is appreciated that in order to provide an alert to the subject regarding for example, glucose measurements, it may be sufficient to indicate a (predetermined minimal) change in the level and/or trend of glucose in the blood. Thus, the system may continuously or repetitively monitor indication of the changes in glucose levels. In some embodiments, the system may perform continuous measurements only upon indication of a significant change such that power is saved and the system operates in "low energy consumption" mode.

Figure 3A:
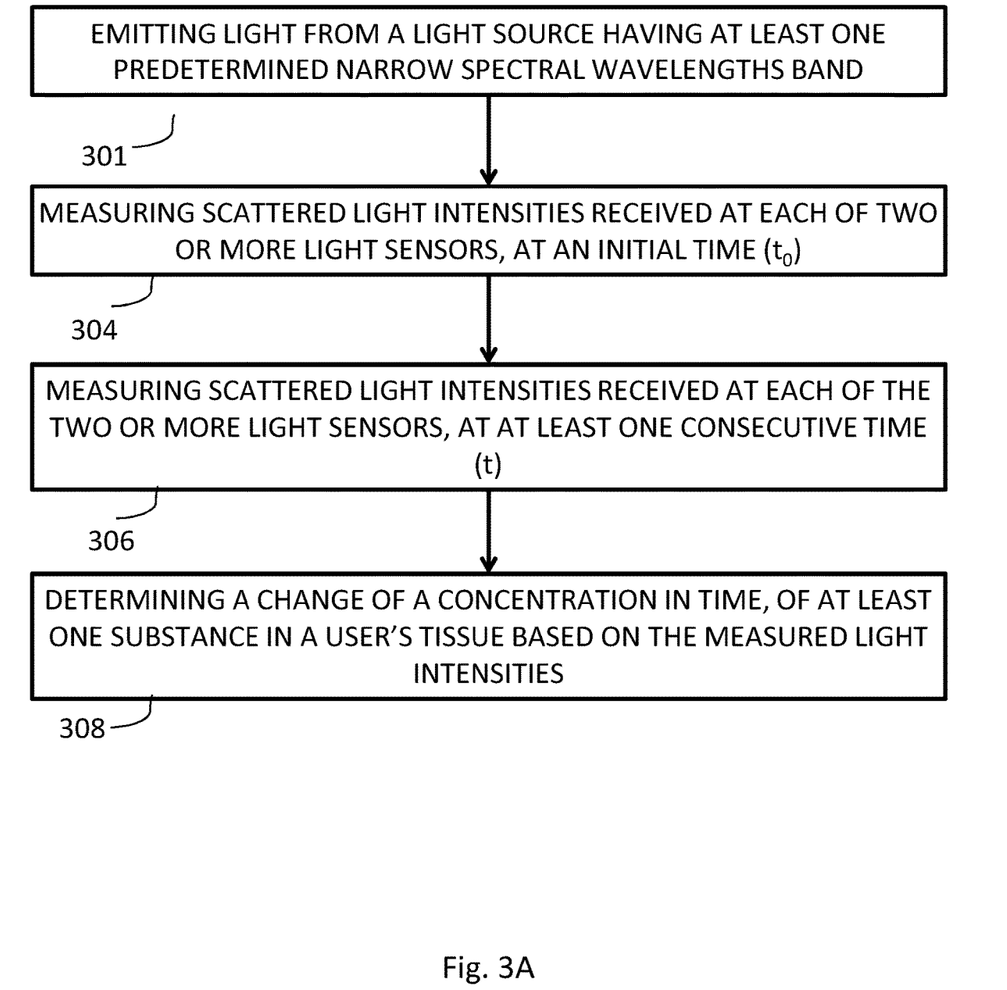
FIGS. 3A and 3B are flowcharts of methods of non-invasive monitoring of physiological condition of a subject, according to some embodiments of the invention.

Reference is now made to FIG. 3A, which shows a flow chart of a method of non-invasive monitoring of physiological measurements of a subject, according to some embodiments of the invention. The method of FIG. 3A may be executed by a controller such as controller 15, device 120 or controller 230 of non-invasive monitoring device 110 and/or non-invasive monitoring system 100. In box 302, at least one light source 210 may be controlled to emit light at least one predetermined narrow spectral wavelengths band. In some embodiments, the controller may control at least one light source 210a-210n to emit light at two or more predetermined narrow spectral wavelength bands $(\lambda_1, \lambda_2 \ldots \lambda_n)$, where each of $\lambda_1, \lambda_2 \ldots \lambda_n$ corresponds to the median wavelength of each band. The light may be emitted at a continuous illumination process or at illumination pules or any combination thereof.

In box 304, scattered light intensities $I_0(\lambda)_1, I_0(\lambda)_2 \ldots I_0(\lambda)_n$ received at each of two or more light sensors 220 $(S_1, \ldots, S_n)$ may be measured at an initial time $(t_0)$. For example, scattered light intensities $I_0(\lambda)_2$ received at sensor $S_2$ may be measured. The measured light intensity may correspond to the concentration level of substance 2 $C_2(0)$ at $t_0$. In some embodiments, scattered light intensities $I_0(\lambda)_2$ may be received from layer $L_2$. In some embodiments, when more than one predetermined narrow spectral wavelength band is emitted, measurements of scattered light intensities may be received at each of the two or more light sensors at the two or more predetermined narrow spectral wavelength bands, at an initial time $(t_0)$.

In box 306, scattered light intensities $I(\lambda,t)_1, I(\lambda,t)_2 \ldots I(\lambda,t)_n$ received at each of two or more light sensors 220 $(S_1, \ldots, S_n)$ may be measured at at least one consecutive time (t). For example, scattered light intensities $I(\lambda,t)_2$ received at sensor $S_2$ may be measured. The measured light intensity may correspond to the concentration level of substance 2 $C_2(t)$ at at least one consecutive time (t). In some embodiments, when more than one predetermined narrow spectral wavelength band is emitted, measurements of scattered light intensities may be received at each of the two or more light sensors at the two or more predetermined narrow spectral wavelength bands, at at least one consecutive time (t). In some embodiments, the at least one consecutive time (t) may include continuous measurements over time (t) or one or more single measurements received at various times $(t_1, t_2 \ldots t_p)$.

In box 306, a change of a concentration $C_i(t)$ in time, of at least one substance in a user's tissue may be determined based on the measured light intensities. For example, the controller may use equation (1)

$$\Delta OD(\lambda, t) = -\ln\left(\frac{I(\lambda, t)}{I_0(\lambda)}\right)$$

to calculate the optical density change at a specific narrow spectral wavelength band having a median $\lambda$ wavelength over time. By calculating a plurality optical density changes from a plurality of sensors $(S_1, \ldots, S_n)$ and/or a plurality of narrow spectral wavelength bands $(\lambda_1, \lambda_2 \ldots \lambda_n)$, the controller may than use equation (10) to calculate the change in the scattering and absorbing parameters $\Delta\mu_{a1}(t)+\Delta\mu'_{s1}(t)$ due to changes in the concentrations of one or more substances. The optical path $L(\lambda,t)$ may be known and may depends from the distance d between corresponding light source 210 and light sensor 220. For example, L(λ,t) may be estimated to be about 2d. The controller may then use the detected change to determine a change in the scattering and absorbing parameters calculated by equation (10) and to determine a change in the concentration of one or substances, as shown in equations (3)-(8).

In some embodiments, if the detected change is larger than a threshold value, the controller may determine a physiological condition of subject 10 such as raise in sugar levels in the blood.

Figure 3B:
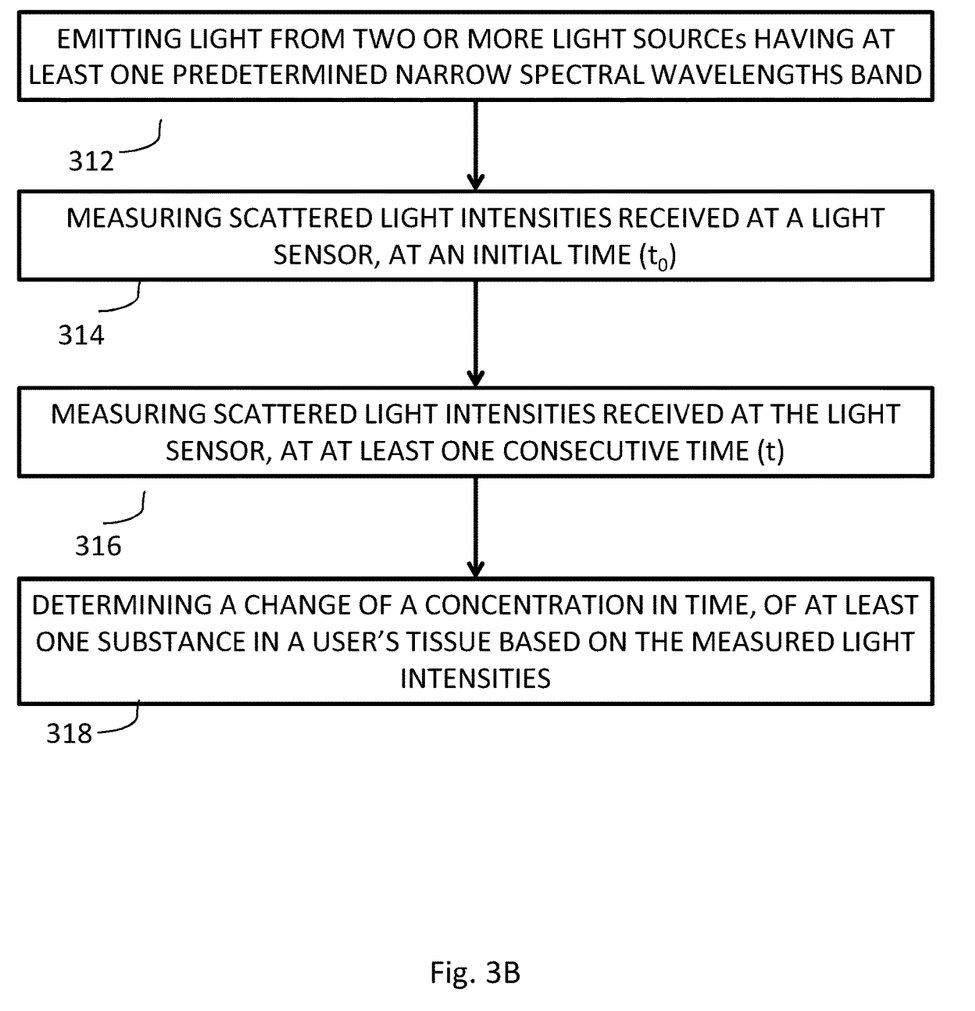

Reference is now made to FIG. 3B, which shows a flow chart for a method of non-invasive monitoring of physiological measurements of a subject, according to some embodiments of the invention. The method of FIG. 3B may be executed by a controller such as controller 15, device 120 or controller 230 of non-invasive monitoring device 110 and/or non-invasive monitoring system 100. In box 312, two or more one light sources 210a-210n may be controlled to emit light at least one predetermined narrow spectral wavelengths band. In some embodiments, the controller may control two or more light sources 210a-210n to emit light at two or more predetermined narrow spectral wavelength bands ($\lambda_1, \lambda_2 \ldots \lambda_n$), where each of $\lambda_1, \lambda_2 \ldots \lambda_n$ corresponds to the median wavelength of each band. The light may be emitted at a continuous illumination process or at illumination pules or any combination thereof.

In box 314, scattered light intensities $I_0(\lambda)_1, I_0(\lambda)_2 \ldots I_0(\lambda)_n$ received at one light sensors 220 may be measured at an initial time ($t_0$). For example, scattered light intensity $I_0(\lambda)_2$ emitted from light source $I_2$ (210b) and received at the sensor 220 may be measured. The measured light intensity may correspond to the concentration level of substance 2 $C_2(0)$ at $t_0$. In some embodiments, scattered light intensity $I_0(\lambda)_2$ may be received from layer $L_2$. In some embodiments, when more than one predetermined narrow spectral wavelength band is emitted, measurements of scattered light intensities may be received at the sensor at the two or more predetermined narrow spectral wavelength bands, at an initial time ($t_0$).

In box 316, scattered light intensities $I(\lambda,t)_1, I(\lambda,t)_2 \ldots I(\lambda,t)_n$ received at light sensor 220 may be measured at at least one consecutive time (t). For example, scattered light intensities $I(\lambda,t)_2$ emitted from light source 210b received at sensor 210 may be measured. The measured light intensity may correspond to the concentration level of substance 2 $C_2(t)$ at at least one consecutive time (t). In some embodiments, when more than one predetermined narrow spectral wavelength band is emitted, measurements of scattered light intensities may be received the light sensor at the two or more predetermined narrow spectral wavelength bands, at at least one consecutive time (t). In some embodiments, the measurements at at least one consecutive time (t) may include continuous measurements over time (t) or one or more single measurements received at various times ($t_1, t_2 \ldots t_p$).

In box 316, a change of a concentration $C_i(t)$ in time, of at least one substance in a user's tissue may be determined based on the measured light intensities. Step 316 of the method of FIG. 3B may be substantially the same as step 306 of the method of FIG. 3A.

Unless explicitly stated, the method embodiments described herein are not constrained to a particular order in time or chronological sequence. Additionally, some of the described method elements may be skipped, or they may be repeated, during a sequence of operations of a method.

Various embodiments have been presented. Each of these embodiments may of course include features from other embodiments presented, and embodiments not specifically described may include various features described herein.

The invention claimed is:

1. A non-invasive device for monitoring physiological condition changes of a subject, comprising:
   at least one light source for emitting light at two or more predetermined narrow spectral wavelength bands onto a living tissue of the subject;
   two or more light sensors ($S_1, \ldots, S_n$), wherein each of the two or more light sensors ($S_1, \ldots, S_n$) corresponds to one or more substances in the living tissue of the subject; and
   a controller configured to:
      control the at least one light source to emit light at the two or more predetermined narrow spectral wavelength bands;
      receive measurements of scattered light intensities received at each of the two or more light sensors ($S_1, \ldots, S_n$), at the two or more predetermined narrow spectral wavelength bands, at an initial time ($t_0$);
      receive measurements of scattered light intensities received at each of the two or more light sensors ($S_1, \ldots, S_n$), at the two or more predetermined narrow spectral wavelength bands, at at least one consecutive time ($t_1$); and
      determine a change of a concentration in time, of the one or more substances to which each of the two or more light sensors ($S_1, \ldots, S_n$) corresponds, wherein the change of the concentration is determined by calculating a set of 'n' equations with 'n' absorption and scattering coefficients for the two or more predetermined narrow spectral wavelength bands, and based on the measured light intensities,
   wherein a distance ($d_1, \ldots, d_n$) of each of the two or more light sensors ($S_1, \ldots, S_n$) from the at least one light source is determined so that a ratio is maximal between an intensity ($I_1, \ldots, I_n$) of light that is scattered by each substance and all other intensities received at each of the two or more sensors ($S_1, \ldots, S_n$) at the determined distance of each of the two or more sensors from the light source.

2. The non-invasive device of claim 1, wherein the distance ($d_1, \ldots, d_n$) of each of the two or more sensors from the at least one light source is further determined according to the depth a layer ($L_1, \ldots, L_n$) of the living tissue in which one or more of the one or more substances is contained.

3. The non-invasive device of claim 1, wherein the distance ($d_1, \ldots, d_n$) of each of the two or more sensors from the at least one light source is further determined using scattering and absorbing parameters of each substance.

4. The non-invasive device of claim 1, wherein each of the two or more predetermined narrow spectral wavelength bands is between 400-2500 nm and has a difference of 5-100 nm between an upper wavelength and a lower wavelength of each band.

5. The non-invasive device of claim 1, further comprising a wearable housing for holding the at least one light source and the two or more light sensors.

6. The non-invasive device of claim 1, comprising two or more light sources for emitting light at the two or more predetermined narrow spectral wavelength bands onto the living tissue, wherein each of the two or more light sources corresponds to a different predetermined narrow spectral wavelength band, and wherein each of the two or more light sources is located at a different distance from the two or more light sensors.

7. A method of non-invasive monitoring of physiological condition changes of a subject, the method comprising:
    emitting light from at least one light source having two or more predetermined narrow spectral wavelength bands;
    measuring scattered light intensities received at each of two or more light sensors, at an initial time ($t_0$);
    measuring scattered light intensities received at each of the two or more light sensors, at at least one consecutive time ($t_1$); and
    determining a change of a concentration in time, of one or more substances in a user's tissue to which each of the two or more light sensors ($S_1, \ldots, S_n$) corresponds, wherein the change of the concentration is determined by calculating a set of 'n' equations with 'n' absorption and scattering coefficients for the two or more predetermined narrow spectral wavelength bands, and based on the measured light intensities,
    wherein each of the two or more light sensors ($S_1, \ldots, S_n$) corresponds to the one or more substances in a living tissue of the subject and is configured to measure a change in a concentration of the specific substances to which the sensor corresponds, and
    wherein a distance ($d_1, \ldots, d_n$) of each of the two or more sensors from the at least one light source is determined so that a ratio is maximal between an intensity ($I_1, \ldots, I_n$) of light scattered by each specific substance and all other intensities received at each of the two or more sensors ($S_1, \ldots, S_n$) at the determined distance of each of the two or more sensors from the light source.

8. A non-invasive device for monitoring physiological condition changes of a subject, comprising:
    one light sensor (S);
    two or more light sources ($l_1, \ldots, l_n$) for emitting light at two or more predetermined narrow spectral wavelength bands onto a living tissue of the subject, wherein each of the two or more light sources ($l_1, \ldots, l_n$) corresponds to one or more substances in the living tissue of the subject; and
    a controller configured to:
        control the two or more light sources ($l_1, \ldots, l_n$) to emit light at the two or more predetermined narrow spectral wavelength bands;
        receive measurements of scattered light intensities received at the light sensor, at the two or more predetermined narrow spectral wavelength bands, at an initial time ($t_0$);
        receive measurements of scattered light intensities received at the light sensor, at the two or more predetermined narrow spectral wavelength bands, at at least one consecutive time ($t_1$); and
        determine a change of a concentration in time, of the one or more substances to which each of the two or more light sources ($l_1, \ldots, l_n$) corresponds, wherein the change of the concentration is determined by calculating a set of 'n' equations with 'n' absorption and scattering coefficients for the two or more predetermined narrow spectral wavelength bands, and based on the measured light intensities,
    wherein a distance ($d_1, \ldots, d_n$) of sensor from the two or more light sources is determined so a ratio between the intensity ($I_1, \ldots, I_n$) of light that is scattered by each substance and all other intensities received at each of the two or more sensors is maximal at the determined distance from the light source.

9. The non-invasive device of claim 8, wherein the distance ($D_1, \ldots d_n$) of each of the two or more light sources from the light sensor is further determined according to the depth a layer ($L_1, \ldots, L_n$) of the living tissue in which one or more of the one or more substances is contained.

10. The non-invasive device of claim 8, wherein the distance ($d_1, \ldots, d_n$) of each of the two or more light sources from the light sensor is further determined using scattering and absorbing parameters of each substance.

11. The non-invasive device of claim 8, wherein each of the two or more predetermined narrow spectral wavelength bands is between 400-2500 nm and has a difference of 5-100 nm between an upper wavelength and a lower wavelength of each band.

12. The non-invasive device of claim 8, further comprising a wearable housing for holding the two or more light sources and the light sensor.

* * * * *